United States Patent [19]

Maldonado et al.

[11] 4,374,282

[45] Feb. 15, 1983

[54] ETHERS OF POLYOLS, THEIR PREPARATION AND USE

[75] Inventors: Paul Maldonado, St. Symphorien D'Ozon; Robert Nouguier, Plan de Cuques; Jean-Claude Fayard, Lyons; Robert Léger, Grigny, all of France

[73] Assignee: Elf France, Paris, France

[21] Appl. No.: 197,205

[22] Filed: Oct. 15, 1980

[30] Foreign Application Priority Data

Oct. 15, 1979 [FR] France ................................ 79 25559

[51] Int. Cl.$^3$ .............................................. C07C 41/01
[52] U.S. Cl. .................................. 568/672; 252/52 R
[58] Field of Search ....................... 252/52 R; 568/672

[56] References Cited

U.S. PATENT DOCUMENTS

| | | | |
|---|---|---|---|
| 1,922,459 | 8/1933 | Schmidt et al. | 252/52 R |
| 2,951,094 | 8/1960 | Hefner et al. | 252/52 R X |
| 2,973,388 | 2/1961 | Reimschneider | 252/52 R X |
| 3,840,605 | 10/1974 | Gordon | 260/614 R |
| 3,914,320 | 10/1975 | Gordon | 260/611 A |
| 3,992,432 | 11/1976 | Napier et al. | 260/454 X |

FOREIGN PATENT DOCUMENTS

| | | | |
|---|---|---|---|
| 928088 | 6/1968 | Canada | 568/672 |
| 1473024 | 5/1977 | United Kingdom . | |
| 1532684 | 11/1978 | United Kingdom . | |

OTHER PUBLICATIONS

Weber et al., "Phase Transfer Catalysis in Organic Synthesis," 1977, pp. 73–84.

*Primary Examiner*—Andrew Metz
*Attorney, Agent, or Firm*—Burgess, Ryan and Wayne

[57] ABSTRACT

Ethers of polyols are prepared by reaction of a polyol and an organic chloride in a two phase medium in the presence of a phase transfer catalyst. The ethers of polyols are useful as synthetic lubricants, as lubricant bases, as lubricant additives and as fuel additives.

9 Claims, No Drawings

ETHERS OF POLYOLS, THEIR PREPARATION AND USE

BACKGROUND OF THE INVENTION

The present invention relates to new lubricating compositions comprising mixtures of hydrocarbon oils and ethers of polyols.

Modern lubricating technology has developed a need for increasingly larger quantities of lubricating compositions with good flow properties at low temperatures, which have suitable viscosities at high temperatures and low volatility.

In the field of lubrication of internal combustion engines, "multigrade" oils are used. The multigrade oils are based on mineral lubricating oils containing viscosity index improvers which modify the viscosity index to meet the requirements for classification for service in summer and winter according to the "SAE" classes of multigrade oils.

The behavior of the low viscosity, mineral-oil-base multigrade oils is not entirely satisfactory. The agents used to improve the viscosity index, for example, esters of polyacrylic or polymethacrylic acids are generally mixed with mineral oil bases which have a low viscosity high volatility and insufficient heat stability.

In addition, the viscosity index improving agents are not stable under the shear forces which arise in service.

The viscosity index improving agents have a detrimental effect on the heat stability of the oil. The loss in heat stability is compensated for by an increase in the amounts of inhibitors and dispersant additives which must be incorporated into the lubricating compositions.

Lubricants having a base of bicarboxylic acid esters, such as alkyl esters of adipic or sebacic acid and lubricants having a base of esters of polyols such as pentaerythritol, trimethylol propane or neopentyl glycol with fatty acids having from about 8 to about 16 carbon atoms mixed with mineral oils have been known in the field of lubrication. In general these esters have problems with wear.

The use of liquid polymers of butylenes, isobutylenes or olefins, such as polydecene, for special purposes, in which lubricants free of mineral bases are required, are known. These polymer oils are characterized by low heat stability or unsatisfactory lubricating properties.

BRIEF DESCRIPTION OF THE INVENTION

It has now been unexpectedly discovered that heat stable lubricants having low volatility, are obtained by use of ethers of polyols resulting from the condensation of alcohols, such as, pentaerythritol, the trimethylolalkanes and neopentylglycol with halides of alkyls having from 1 to 22 carbon atoms and preferably, 6 to 16 carbon atoms. The ethers of polyols can be utilized alone or admixed with mineral oils or other lubricating compositions.

The alkyl ethers of polyols can also be used to improve the properties of liquid combustible hydrocarbons, such as, gasoline, kerosene, jet fuels, heavy and light fuel oils, gasoils and heavy distillates. The alkyl ethers of polyols improve the combustion properties of the combustibles and prolong the useful life of the feed components, such as pumps, injectors and distributors.

The alkyl ethers of polyols are advantageously used at concentrations of from 0.1 to 100% by weight in the lubricating compositions and from 0.001% to 5% by weight in the liquid combustibles. They can also comprise synthetic lubricants or be used alone without mineral bases or other products.

The alkyl ethers of the present invention which are useful in lubricating formulations and as fuel additives are of the formula:

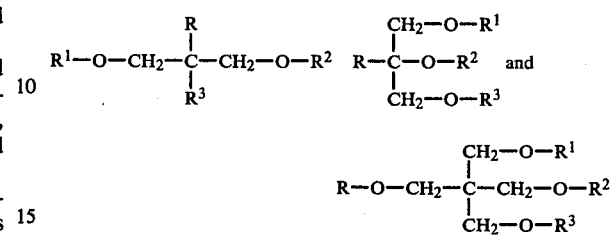

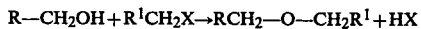

wherein R, $R^1$, $R^2$ and $R^3$ are independently selected alkyl moieties having from 1 to about 22 carbon atoms and preferably, 6 to 16 carbon atoms. The alkyl moieties can be straight chain or branched.

DETAILED DESCRIPTION OF THE INVENTION

The synthesis of organic alkyl ethers by the condensation of a mono-alcohol and an alkyl halide is known in the literature. The condensation reaction can be represented by the following expression:

$$R-CH_2OH + R^1CH_2X \rightarrow RCH_2-O-CH_2R^1 + HX$$

where X is Cl, Br or I and R and $R^1$ are as defined above.

The Williamson reaction for preparation of ethers according to the expression is one example. However, the Williamson reaction requires the prior preparation of an alcholate $RO^-$ by the reaction of an alcohol with metallic sodium, sodium hydride, or sodium amide, followed by the reaction of the alcoholate with an alkyl halide in a polar aprotic solvent such as hexamethylphosphoramide (H.M.P.A.) or dimethyl formamide. The reagents and the solvents are expensive for use on an industrial scale.

When the reaction scheme is used for the synthesis of ethers of polyols by reaction of alkyl halides with polyhydroxy organic compounds such as pentaerythritol, trimethylol propane or neopentylglycol, a mixture of partially etherified products is produced. The process has very low selectivity for completely etherified products. The selectivity for completely etherified products is particularly low when the alkyl halides have long chain lengths.

It has been unexpectedly discovered that selectivity for complete etherification of polyols can be improved by preparation of the ethers in a two phase process using a phase transfer catalyst. Phase transfer catalysts had heretofore been applied only to the etherification of mono- hydric alcohols (reference: Phase transfer catalysis in organic synthesis, W. P. WEBER, and G. W. GORKEL—Springer Verlag Berlin, Heidelberg, New York 1977).

In the process of the present invention a mixture of the polyol to be etherified with water and an alkaline material such as an alkali or alkaline earth metal hydroxide or alkali metal carbonate is prepared. Alkali metal carbonates and particularly, sodium and potassium carbonate or mixtures thereof are the preferred alkaline materials for practice of the process of the present invention and when these alkali metal carbonates are used, the reaction is conducted in an anhydrous medium. When an alkali or alkaline earth metal hydroxide is used, the reaction is conducted in an aqueous medium. The alkaline material is generally present in excess of one equivalent of alkaline material for each hydroxyl moiety and can be present at 50 to 1000% excess without adversely affecting the process. An aqueous solution of the alkaline material of from about 30 to 70% concentration by weight has been found useful. Preferably an aqueous solution containing from 35 to 55% by weight alkaline material is admixed with the polyol.

The second phase of the two phases utilized in the process comprises an alkyl halide dissolved in an organic solvent which is not miscible with the aqueous phase. The organic solvent is a solvent for the alkyl halide and is substantially unreactive in the process. Alkane solvents such as heptane and octane or aromatic solvents such as benzene, chlorobenzene, toluene and xylene are useful in the present invention. The aromatic solvents being preferred.

A phase transfer agent is incorporated into the two phase reaction system of the present invention. The phase transfer agent assists in carrying the reactants across the phase boundary. Applicants believe that an equilibrium exists between the phase transfer agent and the polyol and alkaline material and the aqueous phase which can be represented by the following formula when the phase transfer agent is an ammonium composition:

$$RO^\ominus Na^\oplus + NR_4^\ominus X^\oplus \rightarrow RO^\ominus NR_4^\oplus \ominus NaX$$

The halogen salt is soluble in the aqueous phase and the $RO^\ominus NR_4^\oplus$ product is soluble in the organic phase and reactive with the alkyl halide. The above equation is a possible mechanism by which the reaction can occur but applicants process is not limited by the existence of the reaction or the postulated intermediates.

The phase transfer agents are effective in catalytic quantities, that is from about 0.5 to 30 molar % and preferably from 1 to 25 molar percent based on the number of functional hydroxy groups in the polyol. The use of catalytic quantities of the phase transfer agent is an advantage of the present invention, more especially as the phase transfer agent is recuperated at 80% after reaction.

The term phase transfer agent refers to, but is not limited to, ammonium or phosphonium salts such as those described by J. DOCKS (ref.: Synthesis, 8, 441 (1973)) or E. V. DEMMLOW (ref.: Angew, Chem. Intern. Ed. 13 (3), 170 (1974)).

The aqueous mixture of alkaline material and polyol, the solution of the alkyl halide in an organic solvent and the phase transfer agent are agitated together and reacted. The mixture can be treated to increase the rate of reaction as is well known in the art. The time for reaction is generally from about 2 to 40 hours and is dependent upon the intensity of agitation, temperature, reactants and amounts and composition of the phase transfer agent present in the reacting mixture. Temperatures in the range of from about 5° to about 200° C. have been found to be useful, although lower and higher temperatures can be effective depending upon the polyol, alkyl halide and phase transfer agent utilized in the process.

A possible reaction scheme can be represented by the following equations when pentaerythritol is the polyol and the phase transfer agent is an ammonium salt.

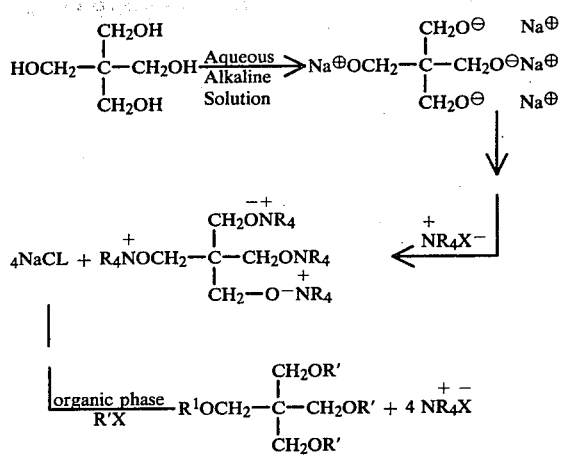

It should be noted that at the end of the condensation, the phase transfer agent is regenerated and can continue to function as a catalyst in the process. The possible mechanism for the reaction is shown for illustrative purposes only so that one skilled in the art can readily understand the function and regeneration of the phase transfer agent. However, applicants' invention is not concerned with the possible reaction mechanism but with the process steps disclosed and the product claimed.

The process of the invention will be better understood by referring to the following non-limiting examples.

EXAMPLE 1

A two-phase reaction medium is introduced into a reactor equipped with mechanical agitation and a heating means. The two phase reaction medium comprises an aqueous phase formed by dissolving 180 g of sodium hydroxide in 160 cc of water and dissolving 40.8 g (0.3 mole) of pentaerythritol in the sodium hydroxide solution. The organic phase comprises 300 cc of benzene in which 92 g (1.2 mole) of allyl chloride is dissolved.

To the two phase medium was added, 10 molar % based on the hydroxy functionality of the polyol, of tetrabutyl ammonium bromide phase transfer agent. The two phase reaction medium was agitated for 12 hours at the reflux temperature of benzene. A yield of 99.7% pentaerythritol tetrallyl ether with a selectivity of 100% was recovered in the organic phase.

EXAMPLE 2

Example 1 was repeated except that the allyl chloride was replaced by 1.2 moles of benzyl chloride. At the end of the 12 hour reaction period pentaerythritol tetrabenzyl ether with a yield of 75.3% and a selectivity of 100% was recovered in the organic phase.

EXAMPLE 3

A two phase medium of Example 1 was prepared with n-hexyl bromide replacing allyl chloride. After refluxing for 48 hours with agitation, pentaerythritol tetrahexyl ether with a yield of 75% and a selectivity of 82.5% was recovered in the organic phase.

Gas chromatography of the product showed that 17.5% of the product is pentaerythritol trihexyl ether and the absence of pentaerythritol monoether and diether.

EXAMPLE 4

Example 3 was repeated but n-heptyl bromide was substituted for the n-hexyl bromide. At the end of 48 hours, pentaerythritol tetraheptyl ether in a yield of 65% and a selectivity of 80% was recovered in the organic phase. The product was characterized by the following physical properties:

| Viscosity at 40° C. in cst: | 12.79 |
|---|---|
| Viscosity at 100° C. in cst: | 3.16 |
| Viscosity Index: | 110 |

EXAMPLE 5

Example 3 was repeated but n-octyl bromide was substituted for n-hexyl bromide. At the end of 48 hours, pentaerythritol tetraoctyl ether in a yield of 70% and a selectivity of 35% was recovered in the organic phase. The secondary product is exclusively pentaerythritol trioctyl ether. Pentaerythritol diether and mono-ether were not present in the product. The mixture of the ethers tri and tetraoctyl ether of pentaerythritol has the following physical properties:

| Viscosity at 40° C. in cst: | 15.17 |
|---|---|
| Viscosity at 100° C. in cst: | 3.65 |
| Viscosity Index: | 118.5 |

EXAMPLE 6

Example 5 was repeated substituting xylene for benzene as the organic solvent. The two phases were reacted with agitation at 120° C. for 24 hours.

At the end of 24 hours, pentaerythritol tetraoctyl ether in a yield of 72% and a selectivity of 87.5% was recovered in the organic phase.

The mixture of pentaerythritol tri and tetraoctyl ethers had the following characteristics:

| Viscosity at 40° C. in cst: | 14.96 |
|---|---|
| Viscosity at 100° C. in cst: | 3.56 |
| Viscosity Index: | 120 |

EXAMPLE 7

Example 6 was repeated substituting methyl tricapryl ammonium chloride in the same proportion for the tetrabutyl ammonium bromide. At the end of the 24 hour reaction period, pentaerythritol tetraoctyl ether in a yield of 70% and a selectivity of 50% was recovered in the organic phase. The product recovered had the same viscosity characteristics as the product of Example 6.

EXAMPLE 8

Example 6 was repeated, substituting tributyl hexadecyl phosphonium bromide ($C_{16}H_{33}P^+-(C_4H_9)_3BR^-$) in the same proportion for the phase transfer agent.

At the end of the 24 hour reaction period, pentaerythritol tetraoctyl ether was recovered in a yield of 30% and a selectivity of 50%. The product had the same viscosity characteristics as those described in Example 6.

EXAMPLE 9

Example 5 was repeated, replacing the pentaerythritol by trimethylol propane.

At the end of the 48 hour reaction period, trioctyl ether of trimethylol propane was recovered in a yield of 80% and a selectivity of 70%.

EXAMPLE 10

Example 9 was repeated but the octyl bromide was replaced by dodecyl bromide.

At the end of the reaction period tridodecyl ether of trimethylol propane was recovered in a yield of 70% and a selectivity of 50%. The secondary product is exclusively didodecyl ether of trimethylol propane to the exclusion of monododecyl ether of trimethylol propane.

The product recovered, (mixture of tri and didodecyl ether of trimethylol propane) had the following viscosity characteristics:

| viscosity at 40° C. in cst: | 19.23 |
|---|---|
| Viscosity at 100° C. in cst: | 4.33 |
| Viscosity Index: | 137 |

EXAMPLE 11

Example 10 was repeated, but the trimethylol propane was replaced by trimethylolhexane.

At the end of the reaction period, tridodecyl ether of trimethylol hexane was recovered in the organic phase in a yield of 65% and a selectivity of 50%. The product recovered had the following characteristics:

| Viscosity at 40° C. in cst: | 19.5 |
|---|---|
| Viscosity at 100° C. in cst: | 4.7 |
| Viscosity Index: | 150 |

EXAMPLE 12

Example 5 was repeated, except that pentaerythritol was replaced by neopentylglycol.

At the end of the reaction period dioctyl ether of neopentylglycol was recovered in the organic phase in a yield of 82% and a selectivity of 95.5%.

EXAMPLES 13 to 24

By way of comparison, the conditions described in Examples 1 to 13 respectively, were repeated, but the phase transfer agent was omitted.

At the end of the reaction times described, the original alkyl halides were recovered in the organic phase, without the formation of the ether.

EXAMPLE 25

A multigrade oil was formulated having the "SAE" characteristics of a 10 W 40 oil with a viscosity at −18° C. between 1300 and 2800 cst and at 98° C. between 13.9 cst and 16.8 cst, containing by weight:
  10% pentaerythritol tetraoctyl ether
  72% of a base oil obtained by distillation of petroleum (kerosene) designated by 175 NS (Neutral Solvent) having a viscosity at 199° C. of 5.72 cst, and a viscosity at 40° C. of 34 cst and a viscosity index of 108

10% by weight of a viscosity additive such as a polymethacrylate dispersant

8% of a mixture of additives comprising:
an antiwear and antioxidant agent of the alkyl dithiophosphate type;
a detergent such as a calcium sulphonate and dispersants.

The oil had excellent antiwear properties in tests of simulated wear conditions in "ignited" engines in normal operation. It also had excellent heat stability and excellent resistance to fouling.

EXAMPLE 26

Results comparable to example 25 were obtained in motor tests using a 10 W 40 oil containing trimethylol propane tridodecyl ether instead of pentaerythritol tetraoctyl ether.

EXAMPLE 27

Comparable performance was obtained with a 10 W 40 oil containing neopentylglycol didodecylether instead of trimethylol propane tridodecyl ether.

EXAMPLE (COMPARATIVE EXAMPLE) 28

When the alkyl ethers of polyols are replaced by the corresponding alkyl esters of polyols, in the formulations of examples 25, 26 and 27, the oil shows good heat stability but poor wear resistance during bench tests.

EXAMPLE 29 (COMPARATIVE EXAMPLE)

The same poor wear resistances were observed when the alkyl ethers of polyols were replaced by the corresponding esters of fatty acids, such as the alkyl adipates.

EXAMPLE 30 (COMPARATIVE EXAMPLE)

When the alkyl ethers of polyols are replaced by polyolefins such as tetradecene in the formulation of examples 25, 26 and 27, the oil provides excellent wear resistance but has poor heat stability as shown by a fouling effect on the engine.

What is claimed:

1. A process for preparing ethers of polyols of the formula

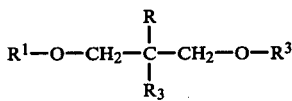

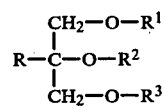

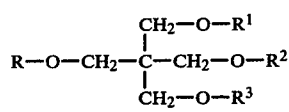

wherein
R, $R^1$, $R^2$ and $R^3$ are independently selected from alkyl radicals having from 1 to 22 carbon atoms, which comprises reacting a solution of an alkyl halide of the formula:

$$R^5 X$$

wherein
$R^5$ can be R, $R^1$, $R^2$ or $R^3$ and X is chloride or bromine and a nonreactive water immiscible organic solvent with a mixture of a polyol of the formula

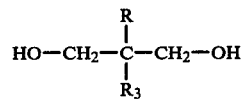

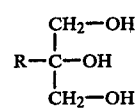

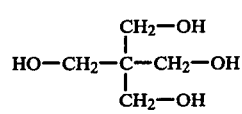

wherein
R and $R_3$ are as defined above and an alkaline aqueous medium in the presence of an effective amount of a phase transfer agent.

2. The process of claim 1 wherein the phase transfer agent is present in an amount of from 1 to 25 molar percent per hydroxyl group.

3. The process of claim 1 wherein the alkaline aqueous medium is a solution of an alkali metal carbonate wherein the alkali metal is selected from the group consisting of sodium, potassium and mixtures thereof.

4. The process of claim 1 further comprising reacting a solution of the alkyl halide in an aromatic solvent with a solution of the polyol in a concentrated aqueous solution of alkali sodium or potassium hydroxide.

5. The process of claim 1 further comprising reacting a solution of the alkyl halide in an aromatic solvent with a solution of the polyol and an anhydrous alkali metal carbonate solution containing from about 25 to 75 percent by weight of alkali metal carbonate based on the weight of water and alkali metal carbonate.

6. The process of claim 5 wherein said alkali metal is selected from sodium and potassium.

7. The process of claim 1 or 5 wherein said organic solvent is selected from the group consisting of benzene, chlorobenzene, toluene and xylene.

8. The process of claim 1 wherein said reaction is conducted at a temperature of from 5° C. to 200° C. for about 2–40 hours.

9. The process of claim 1 wherein said phase transfer agent is selected from the group consisting of ammonium and phosphonium salts.

* * * * *